United States Patent
Elliott et al.

(10) Patent No.: US 6,833,466 B2
(45) Date of Patent: Dec. 21, 2004

(54) FERROUS PICRATE PRODUCED BY AN ISOLATION PROCESS

(75) Inventors: Alan Frederick Elliott, South Melbourne (AU); David M. Stewart, Taylorsville, UT (US); George Riegel, Huntington, WV (US)

(73) Assignee: RDI Construction, South Point, OH (US)

( * ) Notice: Subject to any disclaimer, the term of this patent is extended or adjusted under 35 U.S.C. 154(b) by 0 days.

(21) Appl. No.: 10/746,241

(22) Filed: Dec. 23, 2003

(65) Prior Publication Data

US 2004/0152909 A1 Aug. 5, 2004

Related U.S. Application Data

(63) Continuation-in-part of application No. 10/150,224, filed on May 16, 2002, now Pat. No. 6,670,495, and a continuation-in-part of application No. 10/150,602, filed on May 16, 2002.

(51) Int. Cl.$^7$ .............................. C07F 15/02; C10L 1/22
(52) U.S. Cl. ............................. 556/150; 44/323; 44/367
(58) Field of Search ............................. 556/150; 44/323, 44/367

(56) References Cited

U.S. PATENT DOCUMENTS

| | | | |
|---|---|---|---|
| 2,506,539 A | 5/1950 | Boardman | 44/367 |
| 3,282,858 A | 11/1966 | Simmons et al. | 502/167 |
| 4,073,626 A | 2/1978 | Simmons | 44/367 |
| 4,099,930 A | 7/1978 | Webb | 44/56 |
| 4,129,421 A | 12/1978 | Webb | 44/56 |
| 4,265,639 A | 5/1981 | Scholtz | 44/57 |
| 4,397,654 A | 8/1983 | Hart | 44/53 |
| 4,424,063 A | 1/1984 | Hart | 44/56 |
| 5,087,268 A | 2/1992 | Parish | 44/312 |
| 5,359,103 A | 10/1994 | Elliott et al. | 556/150 |
| 5,562,742 A | 10/1996 | Kolp et al. | 44/367 |
| 5,720,783 A | 2/1998 | Elliott | 44/323 |
| 5,925,153 A | 7/1999 | Riegel | 44/367 |
| 6,670,495 B2 * | 12/2003 | Stewart | 556/150 |
| 2003/0213166 A1 | 11/2003 | Stewart | 44/367 |

FOREIGN PATENT DOCUMENTS

| | | |
|---|---|---|
| DE | 27 59 055 A1 | 12/1979 |
| WO | WO 94/26689 | 11/1994 |

* cited by examiner

Primary Examiner—Porfirio Nazario-Gonzalez
(74) Attorney, Agent, or Firm—TraskBritt

(57) ABSTRACT

A fuel additive containing ferrous picrate produced by a process comprising placing an enclosed iron containing metallic source in a solution of picric acid in a solvent that reacts with iron to produce ferrous picrate. Enclosure of the iron containing metallic source is accomplished with an isolating material. Enclosure may be achieved by completely surrounding the iron containing metallic source with the isolating material or by installing a filter comprising the isolating material on the downstream or the upstream side of a vessel holding the iron containing metallic source and through which the picric acid and liquid containing the picric acid are circulated. If the iron containing metallic source has been completely surrounded, it is placed into the solution. The solution may be agitated. If a filter or filters are utilized, the solution is circulated through the vessel holding the iron containing metallic source.

19 Claims, No Drawings

FERROUS PICRATE PRODUCED BY AN ISOLATION PROCESS

CROSS-REFERENCE TO RELATED APPLICATION

This application is a continuation-in-part of U.S. Ser. No. 10/150,224, filed on May 16, 2002, now U.S. Pat. No. 6,670,495, and a continuation-in-part of co-pending U.S. Ser. No. 10/150,602, filed May 16, 2002, the contents of both of which are incorporated in their entirety by this reference.

TECHNICAL FIELD

This invention relates to the production of a fuel additive using an isolation process to produce ferrous picrate.

BACKGROUND

There are many patents dealing with process for producing ferrous picrate fuel additives. These include U.S. Pat. Nos. 2,506,539, 3,282,858, 4,073,626, 4,099,930, 4,129,421, 4,265,639, 4,424,063, 5,087,268, 5,359,103, 5,720,783, and 5,925,153, each of which is incorporated herein by reference. Only U.S. Pat. Nos. 5,087,268 and 5,925,153, incorporated by reference, employ metallic iron; and these both utilize powdered elemental iron. The large surface area of powdered elemental iron facilitates the desired reaction.

When the iron is freely exposed to the reaction solutions, however, iron particles might remain within the liquid fuel additive that is produced and to cause such additive to degrade over time.

SUMMARY OF THE INVENTION

The present invention isolates a material which contains a metal, such as iron, and which is preferably an iron containing metallic source, from physically entering the product of the reaction while permitting the picric acid to contact and react with the iron.

This is preferably accomplished by enclosing the material containing the metal, such as iron, within any material, designated as the isolating material, that is permeable to the picric acid and liquid containing the picric acid, which has pores of such size that the particles of the material containing the iron cannot pass through such pores, and which comprises material that will not react with the iron, the picric acid, or any other substance within the reactant solution. The iron containing material may comprise an iron containing metallic source in a form such as, for example, powder, filings, objects, particles, nails, wire, steel wool, or combinations of any thereof. In another embodiment, the iron containing material may comprises a non-powdered metallic iron such as filings, objects, particles, nails, wire, steel wool, or combinations of any thereof.

Enclosure can be accomplished by completely surrounding the iron containing metallic source with the isolating material or by installing a filter comprising the isolating material on the downstream, the upstream, or the downstream and the upstream side of a vessel holding the iron containing metallic source and through which the picric acid and liquid containing the picric acid are circulated. The product produced by this process, consequently, does not contain the particles of iron found in fuel additives in accordance with the processes of the prior art.

BEST MODE OF THE INVENTION

The present process may employ any solution of picric acid in a solvent that is known in the art for reacting with an iron containing metallic source to produce ferrous picrate. In one embodiment, the iron containing metallic source reacts with the picric acid to produce ferrous picrate. Preferably, however, a solution that is approximately three percent picric acid (i.e., three grams of picric acid per one hundred milliliters of solvent) is produced by dissolving picric acid in a solvent. Since dry picric acid is explosive, the picric acid is supplied with water. Acceptable solvents that may be used include an aromatic solvent such as benzene, toluene, xylene, a high aromatic petroleum fraction such as Solvent 100, other aromatic solvents and high aromatic petroleum fractions disclosed in the art used for a similar purpose, or any combinations thereof are also acceptable and will hereinafter simply be termed aromatic solvents and high aromatic petroleum fractions. A practical percentage of picric acid which may be achieved within a reasonable time is 2.8 percent. The more picric acid which is dissolved, the better. It is, however, extremely difficult to dissolve significantly more than three percent. The percentage of picric acid which has been dissolved is determined analytically, preferably by titration.

After combining the picric acid with the solvent, water is removed from the solution using any known technique. Preferably, though, settling is allowed to occur so that the water is vertically separate from the solution of picric acid in the solvent. The top layer may be removed by decantation or siphoning, or the bottom layer may be removed by draining. One of the various alternate methods for removal is centrifugal separation; another is azeotropic distillation.

The solution resulting from this preferred mixture is termed a pre-mix (as also, for the purposes of this patent application, is any solution of picric acid in a solvent, after such solution has been dewatered, that is prepared in accordance with the art of preparing ferrous picrate; such solution before dewatering is termed a precursor to the pre-mix solution) and has subsequently added to it an aliphatic alcohol. A non-exclusive list of acceptable aliphatic alcohols includes ethanol, isopropanol, butanol, or any combinations thereof. Butanol is preferred. It is preferable to add the aliphatic alcohol to the pre-mix rather than adding the pre-mix to the aliphatic alcohol in order to prevent the precipitation of some of the dissolved picric acid. Preferably, 25 percent butanol is combined with 75 percent pre-mix on a volume basis.

To the resultant solution, some water, preferably 0.1 to 0.5 percent and most preferably approximately 0.1 percent, is added. This is to control the quantity of water since some water is necessary for the desired reaction to occur, but an excess amount causes instability and degradation in the product. In another embodiment, the amount of water may be about 1 percent. In this embodiment, the reaction would proceed rapidly and the iron concentration may exceed 2,000 parts per million of ferrous iron. The ferrous iron may be diluted with about 3 times the amount of dry solvent to reduce the water content to about 0.25 percent, wherein the ferrous iron would be about 500 parts per million.

Preferably, the solution is agitated after the initial combination of ingredients and each addition of an ingredient.

An iron containing metallic source in the form of powder, filings, other particles, objects or any combinations thereof (e.g., nails, wire, steel wool, etc.) is enclosed within a material, designated the isolating material, that is permeable to the picric acid and liquid containing the picric acid, which has pores of such size that the particles of the material containing the metal cannot pass through such pores, and which is composed of material that will not react with the iron containing metallic source, the picric acid, or any other substance within the reactant solution. In one exemplary embodiment, the metallic may be iron or an iron alloy.

Preferably, the isolating material is cotton cloth. Another non-exclusive example of acceptable material is stainless steel screening of approximately 200 mesh. Other acceptable materials that may be used for the isolating material include, without limitation, polyethylene, polyester, polypropylene, or a combination of polyester and polypropylene. Enclosure may be accomplished by substantially or completely surrounding the iron containing metallic source with the isolating material or by installing a filter comprising the isolating material on the downstream, the upstream, or the downstream and the upstream side of a vessel holding the iron containing metallic source and through which the picric acid and liquid containing the picric acid are circulated.

In another embodiment, the iron containing metallic source is placed in a holder which allows the solution to circulate around the iron containing metallic source. The holder may be a basket having connected sides and a bottom connected to each side and having apertures to permit the solution to flow through the basket and around the iron containing metallic source. One or more walls may optionally be combined with the sides of the basket, with each other or the bottom of the basket to form a unitary structure, e.g., a forming at least one hemisphere in the basket.

If the iron containing metallic source is substantially or completely surrounded, it is placed into the solution. The solution is preferably agitated. If a filter or filters are utilized, the solution is circulated through the vessel holding the iron containing metallic source.

In another exemplary embodiment, a non-powdered metallic iron in the form of filings, other particles, objects or any combinations thereof (e.g., nails, wire, steel wool, etc.) is placed into the solution without utilizing an isolating material. The solution is preferably agitated. If a filter or filters are utilized, the solution is circulated through the vessel holding the iron containing metallic source. In one exemplary embodiment, the metallic may be iron or an iron alloy.

The iron containing metallic source may be cast iron. Typically, but not necessarily, cast iron contains approximately 5 percent (by weight) carbon, silicon, iron carbide, iron sulfide, and iron phosphide.

Preferably, one or more cotton bags containing the metallic iron are attached to the vanes of a stirrer that is used to agitate the solution.

The product resulting from reaction of the picric acid with the wire to produce the ferrous picrate is termed a "concentrate." A preferred concentration of iron in the concentrate is 1425 ppm. It has been experimentally determined, however, that degradation of the product over time is minimized, i.e., stability is maximized, when the solution contains approximately 1.9 percent free (dissolved but unreacted) picric acid and 15 to 16 percent aliphatic alcohol, preferably butanol. A selected concentration of iron less than that of the concentrate is achieved by combining the requisite amounts of concentrate, pre-mix, and aliphatic alcohol to attain the desired concentration of iron while also containing approximately 1.9 percent free picric acid and 15 to 16 percent of the alcohol. For stability, if the water content is higher than 0.25 percent, the water content may be reduced to about 0.25 percent or less by adding dry solvent. This is termed the final product.

Either the concentrate or the final product is appropriately termed a fuel additive.

A further decrease in degradation is caused by the fact that enclosing the powder, filings, or other particles of the iron containing metallic source with the isolating material precludes such powder, filings, or other particles of an iron containing metallic source from being in the concentrate and the final product.

The following illustrates an experiment which may be used as an example of the present process.

EXAMPLE 1

A mixture of 22.5 parts of picric acid and 750 parts of an aromatic solvent such as benzene, toluene, xylene, or a high aromatic petroleum fraction such as Solvesso 100 is agitated in a container until the picric acid is dissolved. Water is removed from the solution. 250 parts of an aliphatic alcohol such as ethanol, isopropanol, butanol, or any combination thereof, and the solution is mixed. 1 part of tap water is added to the solution; and the solution is mixed again. At this point, 5 parts of the iron containing metallic source, such as cast iron filings, containing approximately 95 percent metallic iron, are enclosed within a cotton bag and suspended in the solution. The solution is agitated until the ferrous iron level reaches 1425 ppm, which generally requires several days.

EXAMPLE 2

A mixture of 22.5 parts of picric acid and 750 parts of Solvent 100 was agitated in a container until the picric acid was dissolved. 250 parts of butanol were added to the solution and thoroughly mixed. 1 part of tap water was added to the solution; and the contents were against thoroughly mixed. 8 parts of steel wire were suspended in the solution. The contents of the container were agitated for 1 hour and 35 minutes to produce a ferrous picrate solution containing 1,425 parts per million of ferrous iron.

EXAMPLE 3

A mixture of 22.5 parts of picric acid and 750 parts of Solvent 100 was agitated in a container until the picric acid was dissolved. 250 parts of butanol were added to the solution, and the solution was thoroughly mixed. 1 part of tap water was added to the solution, and the solution was again thoroughly mixed. 3 parts of steel wool were placed in a perforated colander and suspended in the solution. The solution containing the steel wool was agitated until the ferrous iron within the solution reached a concentration of 1425 ppm. The time required was about 8 hours.

As used herein the term "preferable" or "preferably" means that a specified element or technique is more acceptable than another but not that such specified element or technique is a necessity.

We claim:

1. A process for producing ferrous picrate, the process comprising:
   placing a non-powdered metallic iron in a solution comprising picric acid.

2. The process according to claim 1, further comprising:
   agitating the solution comprising the picric acid and the non-powdered metallic iron.

3. The process according to claim 1, wherein the solution comprising the picric acid is produced by a process comprising:
   dissolving the picric acid in a solvent selected from the group consisting of aromatic solvents, high aromatic petroleum fractions, and combinations thereof;

agitating the solvent including the dissolved picric acid;

removing water from the solvent including the dissolved picric acid;

adding an aliphatic alcohol to the solvent including the dissolved picric acid;

agitating the solvent including the dissolved picric acid and the aliphatic alcohol;

adding 0.1 to 0.5 percent water to the solvent including the dissolved picric acid and the aliphatic alcohol; and agitating the solvent including the dissolved picric acid, the aliphatic alcohol and the 0.1 to 0.5 percent water to produce the solution for producing the ferrous picrate.

4. The process according to claim 1, wherein the non-powdered metallic iron is selected from the group consisting of filings, objects, particles, nails, wire, steel wool, and combinations of any thereof.

5. The process according to claim 1, further comprising:

placing the non-powdered metallic iron in an isolating material.

6. The process according to claim 5, wherein the isolating material is selected from the group consisting of cotton cloth, stainless steel, polyester, polyethylene, polypropylene, polyester and polypropylene, and combinations of any thereof.

7. A process for producing a fuel additive containing ferrous picrate, the process comprising:

enclosing an iron containing metallic source in an isolating material; and placing the enclosed iron containing metallic source in a solution for producing the ferrous picrate.

8. The process according to claim 7, wherein the iron containing metallic source is non-powdered.

9. The process according to claim 7, wherein the iron containing metallic source is in a form selected from the group consisting of filings, objects, particles, nails, wire, steel wool, and combinations of any thereof.

10. The process according to claim 7, wherein the iron containing metallic source is cast iron.

11. The process according to claim 7, wherein the enclosing comprises surrounding the iron containing metallic source with the isolating material.

12. The process according to claim 7, further comprising:

agitating the solution containing the enclosed iron containing metallic source.

13. The process according to claim 7, wherein:

the enclosing comprises placing the iron containing metallic source in a vessel having a first filter comprising the isolating material on a downstream side; and the placing the enclosed iron containing metallic source in the solution for producing ferrous picrate comprises circulating the solution for producing the ferrous picrate through the vessel.

14. The process according to claim 13, wherein:

the vessel further comprises a second filter comprising the isolating material on an upstream side.

15. The process according to claim 7, wherein the isolating material is selected from the group consisting of cotton cloth, stainless steel, polyester, polyethylene, polypropylene, polyester and polypropylene, and combinations of any thereof.

16. The process according to claim 7, wherein the solution for producing the ferrous picrate comprises picric acid.

17. The process according to claim 7, wherein:

the solution for producing the ferrous picrate is produced by a process comprising:

dissolving picric acid in a solvent selected from the group consisting of aromatic solvents, high aromatic petroleum fractions, and combinations thereof;

agitating the solvent including the dissolved picric acid;

removing water from the solvent including the dissolved picric acid;

adding an aliphatic alcohol to the solvent including the dissolved picric acid;

agitating the solvent including the dissolved picric acid and the aliphatic alcohol;

adding 0.1 to 0.5 percent water to the solvent including the dissolved picric acid and the aliphatic alcohol; and agitating the solvent including the dissolved picric acid, the aliphatic alcohol and the 0.1 to 0.5 percent water to produce the solution for producing the ferrous picrate.

18. The process according to claim 17, the process further comprising:

adding a pre-mix solution to the solvent including the dissolved picric acid, the aliphatic alcohol, and the 0.1 to 0.5 percent water, wherein the pre-mix solution is produced by the process comprising:

dissolving picric acid in another fraction of solvent selected from the group consisting of aromatic solvents, high aromatic petroleum fractions, and combinations thereof;

removing water from the another fraction of the solvent having the dissolved picric acid; and adding an aliphatic alcohol to the another fraction of the solvent having the dissolved picric acid, such that a resulting solution comprises about 1.9 percent free picric acid and about 15 to 16 percent of the aliphatic alcohol.

19. The process according to claim 7, wherein the isolating material comprises stainless steel screening of approximately 200 mesh.

* * * * *